United States Patent [19]

Burdeska et al.

[11] Patent Number: 5,298,030
[45] Date of Patent: Mar. 29, 1994

[54] PROCESS FOR THE PHOTOCHEMICAL AND THERMAL STABILIZATION OF UNDYED AND DYED OR PRINTED POLYESTER FIBER MATERIALS

[75] Inventors: Kurt Burdeska, Basel; Gerhard Reinert, Allschwil, both of Switzerland; Dieter Reinehr, Kandern, Fed. Rep. of Germany

[73] Assignee: Ciba-Geigy Corporation, Ardsley, N.Y.

[21] Appl. No.: 15,948

[22] Filed: Feb. 10, 1993

[30] Foreign Application Priority Data

Feb. 21, 1992 [CH] Switzerland ............... 541/92-0

[51] Int. Cl.[5] ............... D06P 5/04; D06M 13/325
[52] U.S. Cl. ............................ 8/442; 8/490; 8/566; 8/115.59
[58] Field of Search ............ 8/442, 490, 566, 115.59; 544/219

[56] References Cited

U.S. PATENT DOCUMENTS 4,831,068 5/1989 Reinert et al. ............... 8/442
4,950,304 8/1990 Reinert et al. ............... 8/566
5,197,991 3/1993 Rembold ...................... 8/490

FOREIGN PATENT DOCUMENTS 03528 6/1986 World Int. Prop. O. ............... 8/442
10006 7/1991 World Int. Prop. O. ......... 8/115.59

Primary Examiner—Helene Klemanski
Attorney, Agent, or Firm—George R. Dohmann

[57] ABSTRACT

A process is described for the photochemical and thermal stabilization of undyed and dyed or printed polyester fiber materials, which comprises treating said materials with a compound of formula

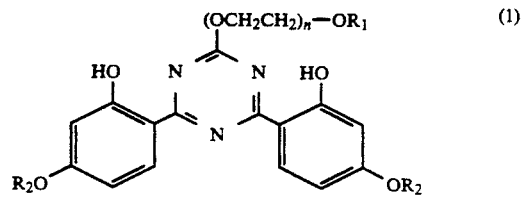

wherein
$R_1$ is hydrogen or $C_1$–$C_5$alkyl,
$R_2$ is $C_1$–$C_{12}$alkyl, and
$n$ is 0 to 5.

Dyeings of superior lightfastness and sublimation fastness on polyester and cellulose acetate are obtained by this process.

8 Claims, No Drawings

PROCESS FOR THE PHOTOCHEMICAL AND THERMAL STABILIZATION OF UNDYED AND DYED OR PRINTED POLYESTER FIBER

The present invention relates to a process for the photochemical and thermal stabilization of undyed and dyed or printed polyester fiber materials.

Dyed or printed polyester fiber materials are damaged by the action of light and, in particular, by the simultaneous action of heat. For use in the automotive field, the provision of an effective protection of undyed and dyed or printed fiber materials from UV radiation is indispensable.

Accordingly, the invention provides a process for the photochemical and thermal stabilization of undyed and dyed or printed polyester fiber materials, which comprises treating said materials with a compound of formula

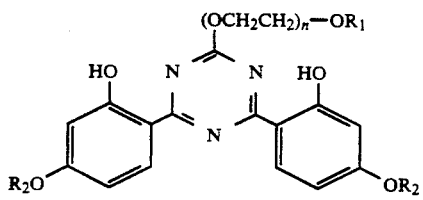

wherein
$R_1$ is hydrogen or $C_1$–$C_5$alkyl,
$R_2$ is $C_1$–$C_{12}$alkyl, and
n is 0 to 5.

$C_1$–$C_{12}$Alkyl groups are straight-chain or branched hydrocarbon radicals, typically methyl, ethyl, n-propyl, isopropyl, n-butyl, sec-butyl, tert-butyl, amyl, isoamyl or tert-amyl, heptyl, octyl, isooctyl, nonyl, undecyl or dodecyl.

It is preferred to use compounds of formula (1), wherein $R_1$ and $R_2$ are each independently of the other $C_1$–$C_4$alkyl.

Among this group of compounds, those compounds are of particular interest wherein $R_1$ and $R_2$ are each independently of the other methyl or ethyl and, most preferably, those compounds wherein $n=1$ to 3.

Typical examples of compounds of formula (1) are:
4,6-bis(2-hydroxy-4-methoxyphenyl)-2-(2-propoxyethoxy)-1,3,5-triazine
4,6-bis(2-hydroxy-4-propoxyphenyl)-2-(2-methoxyethoxy)-1,3,5-triazine
4,6-bis(2-hydroxy-4-ethoxyphenyl)-2-(2-methoxyethoxy)-1,3,5-triazine
4,6-bis(2-hydroxy-4-methoxyphenyl)-2-(2-methoxyethoxy)-1,3,5-triazine
4,6-bis(2-hydroxy-4-methoxyphenyl)-2-(2-ethoxyethoxy)-1,3,5-triazine
4,6-bis(2-hydroxy-4-methoxyphenyl)-2-[2-(2-ethoxyethoxy)ethoxy]-1,3,5-triazine
4,6-bis(2-hydroxy-4-ethoxyphenyl)-2-(2-ethoxyethoxy)-1,3,5-triazine
4,6-bis(2-hydroxy-4-ethoxyphenyl)-2-[2-(2-ethoxyethoxy)ethoxy]-1,3,5-triazine
4,6-bis(2-hydroxy-4-ethoxyphenyl)-2-(2-ethoxy-2-methylethoxy)-1,3,5-triazine
4,6-bis(2-hydroxy-4-methoxyphenyl)-2-{2-[2-(2-ethoxy)ethoxy]ethoxy}-triazine
4,6-bis(2-hydroxy-4-ethoxyphenyl)-2-{2-[2-(2-ethoxy)ethoxy]ethoxy}-1,3,5-triazine
4,6-bis(2-hydroxy-4-ethoxyphenyl)-2-butoxy-1,3,5-triazine.

The compounds of formula (1) are prepared in a manner known per se by reacting a 4,6-bis(2-hydroxy-4-alkoxyphenyl)-1,3,5-triazine of formula

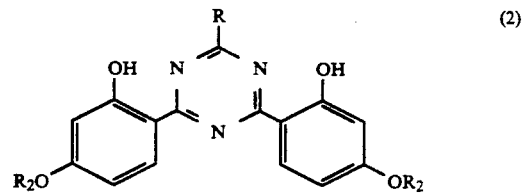

with a compound of formula

according to the following scheme:

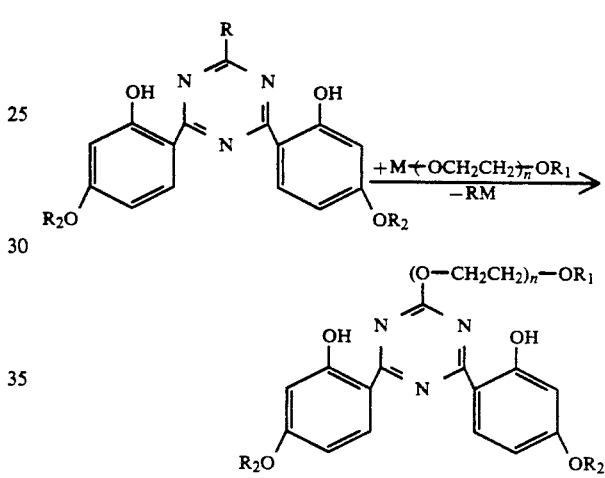

wherein
R is halogen or a radical of formula S-R',
R' is $C_1$–$C_4$alkyl, phenyl or benzyl,
$R_1$ is hydrogen or $C_1$–$C_5$alkyl,
$R_2$ is $C_1$–$C_{12}$alkyl,
M is alkali metal, and
n is 0 to 5.

It is preferred to use starting compounds of formula (2), wherein R is thio-$C_1$–$C_4$alkyl, preferably thiomethyl.

The starting compounds of formula (2) are known, inter alia from CH-436,285. These starting compounds may be prepared substantially in accordance with the process disclosed in EP-A-0,395,938 by reacting cyanuric chloride with $C_1$–$C_4$alkylmercaptan and the corresponding benzenoid compound.

The compounds of formula (3) will be understood as meaning the alkali metal salts of alcohols of general formula

Suitable compounds of formula (3) are polyethylene glycol monoalkyl ethers containing 1 to 5, preferably 1 to 3 ethylene oxide units. Exemplary of such compounds are ethylene glycol monoalkyl ethers such as methyl cellosolve, ethyl cellosolve or propyl cellosolve or diethylene glycol monomethyl ether, diethylene glycol monoethyl ether, diethylene glycol monopropyl ether or diethylene glycol monobutyl ether or the corresponding tri-, tetra- or pentaethylene glycol monoalkyl ethers.

It is also possible to use saturated, branched and unbranched aliphatic $C_1$-$C_5$monoalcohols, typically methanol, ethanol, propanol, isopropanol, butanol, isobutanol, tert-butyl alcohol or amyl alcohol.

It is preferred to use the alcohols in the form of their lithium, potassium or sodium salts, the corresponding sodium alcoholates being preferred.

Some of the compounds of formula (1) are known, inter alia from CH-436,285, and some are also novel compounds.

The novel compounds have the formula

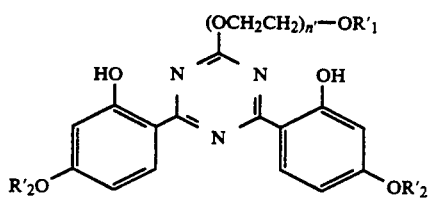

wherein
$R'_1$ is hydrogen or $C_1$-$C_5$alkyl,
$R'_2$ is $C_1$-$C_{12}$alkyl, and
$n'$ is 1 to 5.

Preferred compounds of formula (1') are those wherein $R'_1$ and $R'_2$ are each independently of the other $C_1$-$C_4$alkyl.

Particularly interesting compounds are those wherein $R'_1$ and $R'_2$ are each independently of the other methyl or ethyl and, most especially, those compounds wherein $n'=1$ to 3.

The UV absorbers of this invention are used in an amount of 0.5 to 7.5% by weight, preferably of 0.2 to 3% by weight and, most preferably, of 0.5 to 2% by weight, based on the weight of the fibre material.

The UV absorbers of this invention are sparingly soluble in water are therefore applied in dispersed form. To this end they are milled with an appropriate dispersant, conveniently using quartz balls and an impeller, to a particle size of 1-2 μm.

Suitable dispersants for the UV absorbers of formula (1) are:

acid esters or their salts of alkylene oxide adducts, typically acid esters or their salts of a polyadduct of 4 to 40 mol of ethylene oxide with 1 mol of a phenol, or phosphated polyadducts of 6 to 30 mol of ethylene oxide with 1 mol of 4-nonylphenol, 1 mol of dinonylphenol or, preferably, with 1 mol of compounds which are prepared by addition of 1 to 3 mol of styrenes to 1 mol of phenol,
polystyrene sulfonates,
fatty acid taurides,
alkylated diphenyl oxide mono- or disulfonates,
sulfonates of polycarboxylates,
the polyadducts of 1 to 60 mol of ethylene oxide and/or propylene oxide with fatty amines, fatty acids or fatty alcohols, each containing 8 to 22 carbon atoms in the alkyl chain, with alkylphenols containing 4 to 16 carbon atoms in the alkyl chain, or with trihydric to hexahydric alkanols containing 3 to 6 carbon atoms, which polyadducts are converted into an acid ester with an organic dicarboxylic acid or with an inorganic polybasic acid,
ligninsulfonates, and, most preferably,
formaldehyde condensates such as condensates of ligninsulfonates and/or phenol and formaldehyde, condensates of formaldehyde with aromatic sulfonic acids, typically condensates of ditolyl ether sulfonates and formaldehyde, condensates of naphthalenesulfonic acid and/or naphthol- or naphthylaminesulfonic acids with formaldehyde, condensates of phenolsulfonic acids and/or sulfonated dihydroxydiphenylsulfone and phenols or cresols with formaldehyde and/or urea, as well as condensates of diphenyl oxide-disulfonic acid derivatives with formaldehyde.

Suitable dyes are disperse dyes which are only sparingly soluble in water. They are therefore substantially present in the dye liquor in the form of a fine dispersion. They may belong to different dye classes, including the acridone, azo, andiraquinone, coumarin, methine, perinone, naphthoquinone-imine, quinophthalone, styryl or nitro dyes. Mixtures of disperse dyes may also be used in the practice of this invention.

Polyester fiber material which can be dyed or printed and treated with the cited UV absorbers will be understood as including cellulose ester fibers such as cellulose secondary acetate and cellulose triacetate fibers and, preferably, linear polyester fibers which may also be acid-modified, and which are obtained by the condensation of terephthalic acid with ethylene glycol or of isophthalic acid or terephthalic acid with 1,4-bis(hydroxymethyl)cyclohexane, as well as copolymers of terephthalic and isophthalic acid and ethylene glycol. The linear polyester fiber material hitherto used almost exclusively in the textile industry consists of terephthalic acid and ethylene glycol.

The fiber materials may also be used as blends with each other or with other fibers, typically blends of polyacrylonitrile/polyester, polyamide/polyester, polyester/cotton, polyester/viscose and polyester/wool, and they can be dyed or also printed batchwise or continuously.

The textile material can be in different forms of presentation, preferably as piece goods such as knitgoods or wovens or also as yarn on cheeses, warp beams and the like.

Dyeing is carried out from an aqueous liquor by a continuous or batch process. In batchwise dyeing, the liquor ratio may be chosen over a wide range, typically from 1:4 to 1:100, preferably from 1:6 to 1:50. The dyeing temperature is at least 50° C. and is normally not higher than 140° C. The preferred temperature range is from 80° to 135° C.

In continuous dyeing methods, the dye liquors, which my contain further auxiliaries in addition to the dyes, are applied to the piece goods by padding or slop-padding and developed by thermofixation or HT steaming processes.

Linear polyester fibers and cellulose fibers are preferably dyed by the high temperature process in closed and pressure-resistant apparatus in the temperature range >100° C., preferably in the range from 110° to 135° C., and at normal or elevated pressure. Suitable closed apparatus includes typically circulation dyeing machines such as cheese or beam dyeing machines, winch becks, jet or drum dyeing machines, muff dyeing machines, paddles or jiggers.

For continuous dyeing, padders or lick rollers are used and development is carried out with hot air in stenter frames or in HT steamers.

Cellulose secondary acetate is preferably dyed in the temperature range from 80°-85° C.

When using the novel UV absorbers for dye application, the procedure is such that the fiber material is first treated with these compounds and then dyeing is carried out or, preferably, the fiber material is treated simultaneously in the dyebath with the UV absorber and the dye. The application of the UV absorber can, however, also be made subsequently to the ready prepared dyeing by thermofixation, conveniently at 190°-230° C. over a period of 30 seconds to 5 minutes.

The dye liquors may also contain further ingredients such as dyeing assistants, dispersants, carriers, wool protectives, and wetting agents as well as antifoams.

The dyebaths may also contain mineral acids, typically sulfuric acid or phosphoric acid, or conveniently organic acids, typically aliphatic carboxylic acids such as formic acid, acetic acid, oxalic acid or citric acid and/or salts such as ammonium acetate, ammonium sulfate or sodium acetate. The acids are used in particular to adjust the pH of the liquors used in the practice of this invention to 4-5.

Preferably the fiber material is first run in the bath which contains the dye, the UV absorber and any further auxiliaries and which has been adjusted to pH 4.5-5.5 at 40°-80° C., then the temperature is raised to 125°-130° C. over 10 to 20 minutes, and further treatment is carried out for 15 to 90 minutes, preferably for 30 minutes, at this temperature.

The dyeings are finished by cooling the dye liquor to 50°-80° C., washing off the dyeings with water and, if necessary, reduction clearing them in conventional manner in alkaline medium. The dyeings are then again washed off and dried. When using vat dyes for dyeing the cellulose moiety, the goods are first treated with hydrosulfite at pH 6-12.5, then treated with an oxidising agent and finally washed off.

For producing prints, the novel UV absorbers are mixed in the form of aqueous dispersions with the print pastes. The print paste then contains the UV absorber in an amount of 0.5 to 5%, preferably 1 to 2%, based on the weight of the print paste.

The amount of dye added to the print pastes will depend on the desired shade. Normally amounts of 0.01 to 15% by weight, preferably of 0.02 to 10% by weight, have been found useful.

In addition to containing the dyes and the aqueous dispersion of he UV absorber, the print pastes conveniently contain acid-stable thickeners, preferably of natural origin such as carob bean flour derivatives, especially sodium alginate by itself or in admixture with modified cellulose, preferably with 20 to 25% by weight of carboxymethyl cellulose. If desired, the print pastes may further contain acid donors such as butyrolactone or sodium hydrogen phosphate, preservatives, sequestering agents, emulsifiers, water-insoluble solvents, oxidizing agents or dearating agents.

Particularly suitable preservatives are formaldehyde donors such as paraformaldehyde and trioxane, preferably c. 30 to 40% by weight aqueous formaldehyde solutions. Suitable sequestering agents are sodium nitrilotriacetate, sodium ethylenediaminetetraacetate, preferably sodium polymethaphosphate, more particularly sodium hexamethaphosphate. Emulsifiers are preferably polyadducts of an alkylene oxide and a fatty alcohol, more particularly a polyadduct of oleyl alcohol and ethylene oxide. Water-insoluble solvents are preferably high-boiling saturated hydrocarbons, more particularly paraffins having a boiling range from about 160° to 210° C. (white spirits). Oxidizing agents are typically aromatic nitro compounds, preferably an aromatic mono- or dinitrocarboxylic acid or mono- or dinitrosulfonic acid which may be in the form of an alkylene oxide polyadduct, preferably a nitrobenzenesulfonic acid. Deaerating agents are suitably high-boiling solvents, preferably terpentine oils, higher alcohols, $C_8$-$C_{10}$alcohols, terpene alcohols or deaerating agents based on mineral and/or silicone oils, preferably commercial formulations comprising about 15-25% by weight of a mixture of mineral and silicone oils and about 75-85% by weight of a $C_8$alcohol such as 2-ethyl-n-hexanol.

For printing the fiber materials, the print paste is applied direct to the whole or to a part of the surface, conveniently using printing machines of conventional construction, typically rotogravure, rotary screen printing and surface screen printing machines.

The fiber material is dried after printing in the temperature range up to 150° C., preferably in the range from 80° to 120° C.

The subsequent fixation of the fiber material is usually carried out by a heat treatment, preferably in the temperature range from 100° to 220°. The heat treatment is normally carried out with superheated steam under atmospheric pressure.

Depending on the temperature, fixation is carried out for 20 seconds to 10 minutes, preferably for 4 to 8 minutes.

The prints are also finished in conventional manner by washing off with water, followed by an optional reductive afterclear in alkaline medium, conveniently with sodium dithionite. In this last mentioned case, the prints are again washed off, hydroextracted and dried.

The process of this invention makes it possible to obtain dyeings and prints of superior lightfastness and sublimation fastness on polyester material. A systematic pre- or aftertreatment of the fibre material is not necessary in the inventive process.

In the following working and application Examples percentages are by weight. The amounts of dye and UV absorber are based on pure substance.

PREPARATION OF THE UV ABSORBERS

Example 1

3.5 g (0.15 mol) of sodium are dissolved in 180 ml of propyl cellosolve. With stirring, 18.6 g (0.05 mol) of 2-thiomethyl-4,6-bis(2-hydroxy-4-methoxyphenyl)-1,3,5-triazine are added and the reaction mixture is stirred for 4 hours at 83°-85° C. The reaction mixture is cooled to room temperature and then poured into 200 ml of ice-water and 170 ml of 1N HCl and filtered. The filter product is washed with methanol and dried at 80° C. in a vacuum drier, giving 20.6 g of a pale product of formula

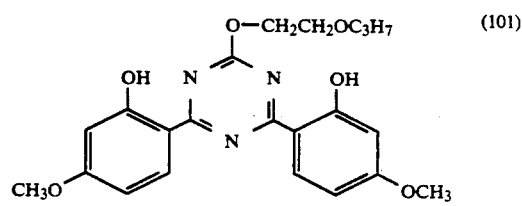

(101)

Yield: 96.4% of theory, mp: 119°-120° C, $\lambda_{max}$: 296/351 nm.

Elemental analysis: found: 61.70% C; 5.9% H; 9.9% N; calcd. as $C_{22}H_{25}N_3O_6$: 61.82% C; 5.89% H; 9.83% N.

Examples 2–14

The following compounds (102) to (114) are prepared in accordance with the general procedure described in Example 1 (Table 1).

TABLE 1

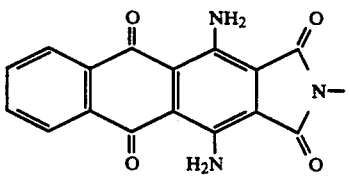

| Compound | $R_1$ | R | Yield [%] | mp [°C] | $\lambda_{max}$ [nm] |
|---|---|---|---|---|---|
| (102) | $C_3H_7$ | $CH_2CH_2OCH_3$ | n.f. | 127–128 | 297/352 |
| (103) | $CH_3$ | $CH_2CH_2OCH_3$ | 97.1 | 190–191 | 296/351 |
| (104) | $CH_3$ | $CH_2CH_2OC_2H_5$ | 96.1 | 155–156 | 296/350 |
| (105) | $CH_3$ | $(CH_2CH_2O)_2C_2H_5$ | 94.4 | 126–127 | 295/350 |
| (106) | $C_2H_5$ | $CH_2CH_2OC_2H_5$ | 93.8 | 161–162 | 297/352 |
| (107) | $C_2H_5$ | $(CH_2CH_2O)_2C_2H_5$ | 75.4 | 133–134 | 297/352 |
| (108) | $C_2H_5$ | $CH_2CH_2OC_3H_7$ | 96.6 | 144–145 | 297/352 |
| (109) | $C_2H_5$ | $CH_2CH_2OCH_3$ | 90.3 | 150–151 | 297/352 |
| (110)* | $CH_3$ | $(CH_2)_7CH_3$ | 79.8 | 110–111 | 295/350 |
| (111) | $CH_3$ | $(CH_2CH_2O)_3C_2H_5$ | 91.3 | 106–107 | 296/351 |
| (112) | $C_2H_5$ | $(CH_2CH_2O)_3C_2H_5$ | 66.5 | 99–100 | 298/353 |
| (113)* | $C_2H_5$ | $(CH_2)_7CH_3$ | 71.8 | 129–130 | 296/351 |
| (114)* | $C_2H_5$ | $C_4H_9$ | 73.8 | 173–174 | 296/351 |

APPLICATION EXAMPLES

Examples 15–29

Use in dyeing

Fifteen 10 g samples of PES tricot are dyed in a HT dyeing machine, e.g. ®Turbomat (supplied by Mathis, Niederhasli) at a liquor ratio of 1:10. The liquors contain 2 g/l of ammonium sulfate, 0.5 g/l of a dyeing auxiliary ®Univadin 3-flex and the dyes of formulae (I) to (IV) in the following amounts:

0.05% of the dye of formula

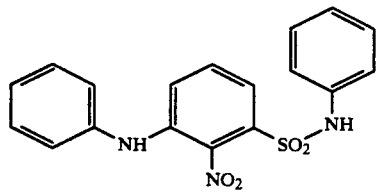

(I)

0.025% of the dye of formula

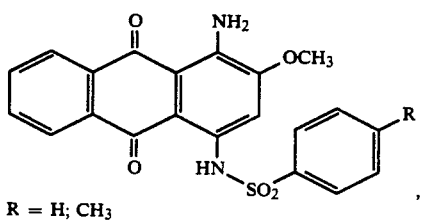

R = H; $CH_3$ (II)

0.03% of the dye of formula

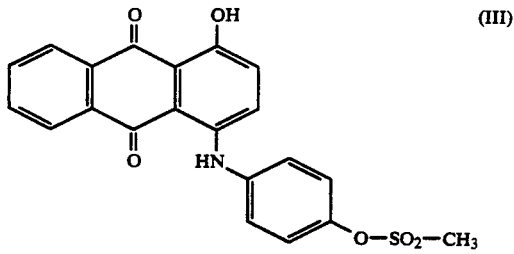

(III)

and 0.025% of the dye of formula (IV)

—$(CH_2)_3$—$OCH_3$ (142 parts)
—$(CH_2)_3$—$O(CH)_2OCH_3$ (58 parts).

Whereas liquor 1 contains no further ingredients, 2% of each of the formulated compounds (101) to (114) are added to liquors 2 to 15.

The UV absorbers are formulated before addition to the dye liquor or as print paste. This is done by milling
the respective compounds,
the naphthalenesulfonic acid/formaldehyde condensate used as dispersant in the ratio 1:1,
the 2–4-fold amount of water, and
the 4-fold amount of quartz balls ($\phi 1$ mm)
with an impeller until the product has a particle size of 1–2 μm. The dispersion is separated with a fine mesh sieve and stabilised with 0.5% of carboxymethyl cellulose and adjusted to 30%.

The tricot samples are dyed in the dispersed liquors in pressure bombs. The samples are put into the liquors at 70° C. and after a treatment time of 5 minutes heated for 10 minutes to 100° C. and finally for 20 minutes to 130° C. Dyeing is carried out for 30 minutes at this temperature and then, after cooling to 50° C., the dyed samples are rinsed with warm and cold water. A reductive after-clear is subsequently carried out at 70° C. for 30 minutes with 2 ml/l of aqueous sodium hydroxide of 36 Bé and 3 g/l of sodium dithionite. Afterwards the samples are again washed off with warm and cold water, centrifuged and dried.

The lightfastness properties are determined by irradiating the dyeings in accordance with DIN 75.202 (FAKRA) and SAE J 1885. The results are reported in Table 2.

TABLE 2

| Dyeing (liquor) | Lightfastness according to | | |
|---|---|---|---|
| | FAKRA 3 cycles | FAKRA 5 cycles | SAE 420 KJ |
| no addition | 2–3 | 2 H | 1–2 |
| (1) + compound (101) | 4 | 3–4 H | 3 H |
| (2) + compound (102) | 4 | 3–4 H | 3 H |
| (3) + compound (103) | 4 | 3–4 H | 3 H |
| (4) + compound (104) | 4 | 3–4 H | 3 H |
| (5) + compound (105) | 4 | 3–4 H | 3 H |
| (6) + compound (106) | 4 | 3–4 H | 3 H |
| (7) + compound (107) | 4 | 3–4 H | 3 H |

TABLE 2-continued

| Dyeing (liquor) | Lightfastness according to | | |
|---|---|---|---|
| | FAKRA 3 cycles | FAKRA 5 cycles | SAE 420 KJ |
| (8) + compound (108) | 4 | 3-4 H | 3 H |
| (9) + compound (109) | 4 | 3-4 H | 3 H |
| (10) + compound (110) | 3-4 | 3 H | 2-3 H |
| (11) + compound (111) | 3-4 | 3 H | 2-3 |
| (12) + compound (112) | 3-4 | 3 H | 2-3 |
| (13) + compound (113) | 4 | 3 | 2-3 |
| (14) + compound (114) | 4 | 2-3 | 2-3 |

Table 2 demonstrates that the use of the UV absorbers (101)-(114) markedly enhances the lightfastness properties of the pale grey dyeings obtained.

Examples 30-35

Use for printing

Print pastes of the following composition are used for printing PES automobile upholstery:
750 parts of a stock thickening comprising
9 parts of starch ether as thickener
18 parts of sodium alginate as thickener
3.75 parts of sodium dihydrogen phosphate
2.48 parts of sodium chlorate and
716.77 parts of water.
This stock thickening is mixed with
6.4 parts of the dye mixture consisting of
2.0 parts of the dye of formula

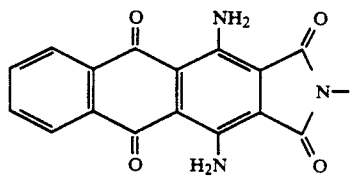

—(CH$_2$)$_3$—OCH$_3$
—(CH$_2$)$_3$—O(CH$_2$)$_2$OCH$_3$
ratio c. 1:1

1.4 parts of the dye of formula

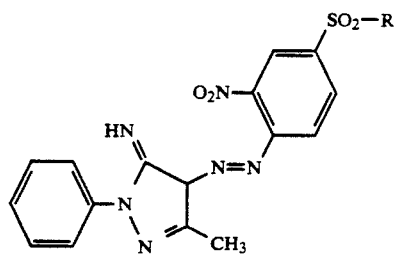

R = —CH$_3$
—C$_2$H$_5$
ratio c. 1:1

2.0 parts of the dye of formula

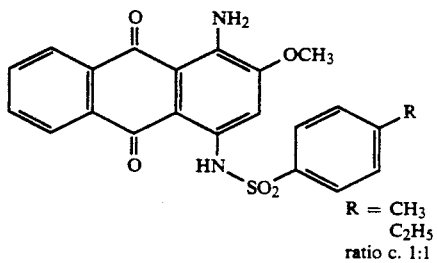

R = CH$_3$
C$_2$H$_5$
ratio c. 1:1 and 1.0 part of the dye of formula

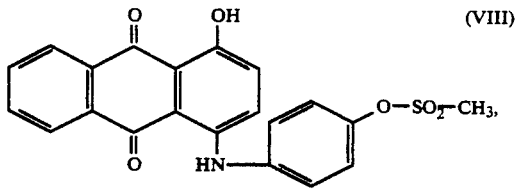

213.6 parts of water, and
30 parts of the dispersed 30% UV absorber formulation of Example 15 containing each of the compounds (101), (103), (109), (113) and (114).

The pre-cleaned PES tricot samples are printed with these print pastes on a Zimmer printing table (supplied by Zimmer, Klagenfurt/Austria). These samples are dried and steamed with superheated steam at 180° C. for 8 minutes. The samples are then rinsed with cold water and given a reductive afterclear at 70° C. for 30 minutes in baths containing 2 ml/l of aqueous sodium hydroxide of 36° Bé and 3 g/l of sodium dithionite. The samples are rinsed with warm and cold water, centrifuged and dried at 80° C. They are then tested for their lightfastness properties in accordance with SN-ISO 105 B02 (XENON), DIN 75.202 (FAKRA), and according to SAE J 1885 (SAE). The results are reported in Table 3.

TABLE 3

| Prints | Lightfastness properties according to | | | |
|---|---|---|---|---|
| | XENON 800 h | FAKRA 4 cycles | SAE 489 KJ | SAE 600 KJ |
| no addition | 7-8 | 1-2 RH | 1 RH | 1 RH |
| (1) + compound (101) | 7-8 | 4 | 3-4 H | 3-4 H |
| (2) + compound (103) | 7-8 | 4 | 3-4 H | 3 H |
| (3) + compound (109) | 8 | 4 | 3-4 H | 3 H |
| (4) + compound (113) | 7-8 | 3 | 2-3 | 2-3 |
| (5) + compound (114) | 8 | 3-4 H | 3 H | 2-3 H |

The results reported in Table 3 show that the UV absorbers effect a marked enhancement of the hot lightfastness properties.

What is claimed is:

1. A process for photochemical and thermal stabilization of undyed and dyed or printed polyester fiber materials, which comprises treating said materials with a compound of formula

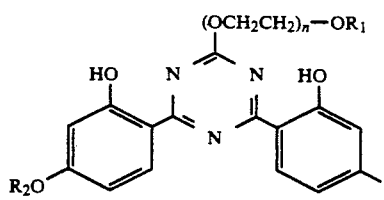

wherein
R$_1$ is hydrogen or C$_1$-C$_5$alkyl,
R$_2$ is C$_1$-C$_{12}$alkyl, and
n is 0 to 5.

2. A process according to claim 1, wherein R$_1$ and R$_2$ are each independently of the other C$_1$-C$_4$alkyl.

3. A process according to claim 1, wherein R$_1$ and R$_2$ are each independently of the other methyl or ethyl.

4. A process according to claim 1, wherein n=1 to 3.

5. A process according to claim 1, wherein the compound of formula (1) is used in an amount of 0.5 to 7.5% by weight, based on the fiber material.

6. A process according to claim 1, wherein the compound of formula (1) is added directly to the dyebath or to the padding liquor for dye application.

7. A process according to claim 1, wherein the compound of formula (1) is mixed with the print paste for print application.

8. The fiber material treated by a process as claimed in claim 1.

* * * * *